(12) United States Patent
Li et al.

(10) Patent No.: US 12,332,428 B2
(45) Date of Patent: Jun. 17, 2025

(54) COMB-DRIVEN MEMS RESONANT SCANNER WITH FULL-CIRCUMFERENTIAL RANGE AND LARGE OUT-OF-PLANE TRANSLATIONAL DISPLACEMENT

(71) Applicant: THE REGENTS OF THE UNIVERSITY OF MICHIGAN, Ann Arbor, MI (US)

(72) Inventors: Haijun Li, Ann Arbor, MI (US); Thomas D. Wang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 674 days.

(21) Appl. No.: 17/439,728

(22) PCT Filed: Mar. 18, 2020

(86) PCT No.: PCT/US2020/023397
§ 371 (c)(1),
(2) Date: Sep. 15, 2021

(87) PCT Pub. No.: WO2020/191077
PCT Pub. Date: Sep. 24, 2020

(65) Prior Publication Data
US 2022/0155584 A1     May 19, 2022

Related U.S. Application Data
(60) Provisional application No. 62/820,032, filed on Mar. 18, 2019.

(51) Int. Cl.
*G02B 26/10* (2006.01)
*A61B 1/00* (2006.01)
(Continued)

(52) U.S. Cl.
CPC ........ *G02B 26/101* (2013.01); *A61B 1/00172* (2013.01); *B81B 3/0043* (2013.01);
(Continued)

(58) Field of Classification Search
CPC .............. G02B 26/101; G02B 26/0841; A61B 1/00172; B81B 3/0043; B81B 2201/042;
(Continued)

(56) References Cited

U.S. PATENT DOCUMENTS 5,969,848 A * 10/1999 Lee ........................ G02B 26/06
359/291
6,008,925 A * 12/1999 Conemac ............. G02B 26/122
372/24

(Continued)

FOREIGN PATENT DOCUMENTS

| KR | 20110107154 A | 9/2011 |
|---|---|---|
| SG | 194332 A1 | 11/2013 |

OTHER PUBLICATIONS

Duan et al., MEMS-based multiphoton endomicroscope for repetitive imaging of mouse colon, Biomed Opt Express, 2015. 6(8): p. 3074-83.
(Continued)

*Primary Examiner* — Sharrief I Broome
(74) *Attorney, Agent, or Firm* — MARSHALL, GERSTEIN & BORUN LLP

(57) ABSTRACT

A scanning assembly for an optical instrument includes a reflector and a folded-beam spring assembly coupled to the reflector for deflecting the reflector for beam scanning. A lever suspension assembly is coupled to the folded-beam spring assembly and provides torsional movement of the reflector for beam scanning over a two-dimensional region, allowing for large total scan angles and large vertical displacements.

14 Claims, 16 Drawing Sheets

(51) Int. Cl.
*B81B 3/00* (2006.01)
*G02B 26/08* (2006.01)

(52) U.S. Cl.
CPC .... *G02B 26/0841* (2013.01); *B81B 2201/042* (2013.01); *B81B 2203/0136* (2013.01); *B81B 2203/0163* (2013.01); *B81B 2203/04* (2013.01); *B81B 2203/053* (2013.01); *B81B 2203/058* (2013.01)

(58) Field of Classification Search
CPC .... B81B 2203/0136; B81B 2203/0163; B81B 2203/04; B81B 2203/053; B81B 2203/058
USPC ........................................................ 359/199.4
See application file for complete search history.

(56) References Cited

U.S. PATENT DOCUMENTS

| | | | |
|---|---|---|---|
| 6,091,537 A | | 7/2000 | Sun et al. |
| 6,246,504 B1* | | 6/2001 | Hagelin ............... G02B 26/105 |
| | | | 359/201.1 |
| 7,142,352 B2 | | 11/2006 | Pardo et al. |
| 7,202,898 B1* | | 4/2007 | Braun ................... G01S 17/894 |
| | | | 348/308 |
| 7,388,700 B1* | | 6/2008 | Odhner ................. G02B 7/1821 |
| | | | 359/224.1 |
| 7,482,730 B2 | | 1/2009 | Davis et al. |
| 7,636,101 B2 | | 12/2009 | Sprague et al. |
| 2002/0047493 A1 | | 4/2002 | Jeong et al. |
| 2002/0097477 A1 | | 7/2002 | Hagelin et al. |
| 2005/0002084 A1* | | 1/2005 | Wan ...................... B81B 3/0035 |
| | | | 359/291 |
| 2006/0227409 A1* | | 10/2006 | Pardo ................. G02B 26/0841 |
| | | | 359/298 |
| 2007/0290572 A1* | | 12/2007 | Park ................... G02B 26/0841 |
| | | | 310/309 |
| 2009/0028407 A1* | | 1/2009 | Seibel .................. A61B 1/0627 |
| | | | 382/131 |
| 2010/0296146 A1* | | 11/2010 | Krastev ............. G02B 26/0833 |
| | | | 359/224.1 |
| 2011/0080627 A1* | | 4/2011 | He ..................... G02B 26/0841 |
| | | | 359/224.1 |
| 2018/0039075 A1 | | 2/2018 | Lim et al. |
| 2018/0059406 A1* | | 3/2018 | Torkkeli ............... G02B 26/105 |
| 2018/0356629 A1 | | 12/2018 | Wang et al. |

OTHER PUBLICATIONS

European Patent Application No. 20774405.3, Extended European Search Report, dated Jul. 11, 2022.

Fan et al., Video-rate scanning two-photon excitation fluorescence microscopy and ratio imaging with cameleons, Biophys J, 1999. 76(5): p. 2412-20.

Fu et al., Nonlinear optical endoscopy based on a double-clad photonic crystal fiber and a MEMS mirror, Opt Express, 2006. 14(3): p. 1027-32.

Herrera-May et al., Recent Advances of MEMS Resonators for Lorentz Force Based Magnetic Field Sensors: Design, Applications and Challenges. Sensors (Basel), 2016. 16(9).

International Application No. PCT/US2020/023397, International Search Report and Written Opinion, mailed Jun. 18, 2020.

Kumar et al., Dual-view plane illumination microscopy for rapid and spatially isotropic imaging, Nat Protoc, 2014. 9(11): p. 2555-73.

Li et al., Integrated monolithic 3D MEMS scanner for switchable real time vertical/horizontal cross-sectional imaging, Opt Express, 2016. 24(3): p. 2145-55.

Liu et al., Mems-Based 3d Confocal Scanning Microendoscope Using Mems Scanners for Both Lateral and Axial Scan, Sens Actuators A Phys, 2014. 215: p. 89-95.

Piyawattanametha et al., Fast-scanning two-photon fluorescence imaging based on a microelectromechanical systems two-dimensional scanning mirror, Opt Lett, 2006. 31(13): p. 2018-20.

Saggau, New methods and uses for fast optical scanning, Curr Opin Neurobiol, 2006. 16(5): p. 543-50.

Sun et al., 3D in vivo optical coherence tomography based on a low-voltage, large-scan-range 2D MEMS mirror. Opt Express, 2010. 18(12): p. 12065-75.

* cited by examiner

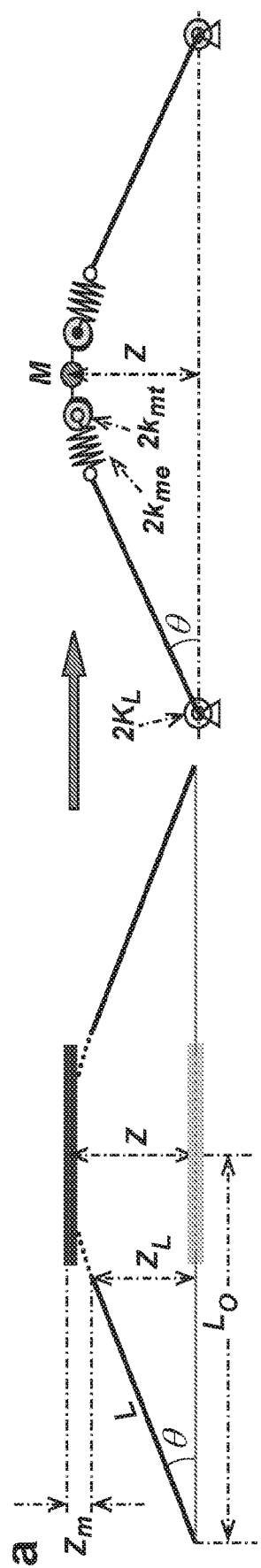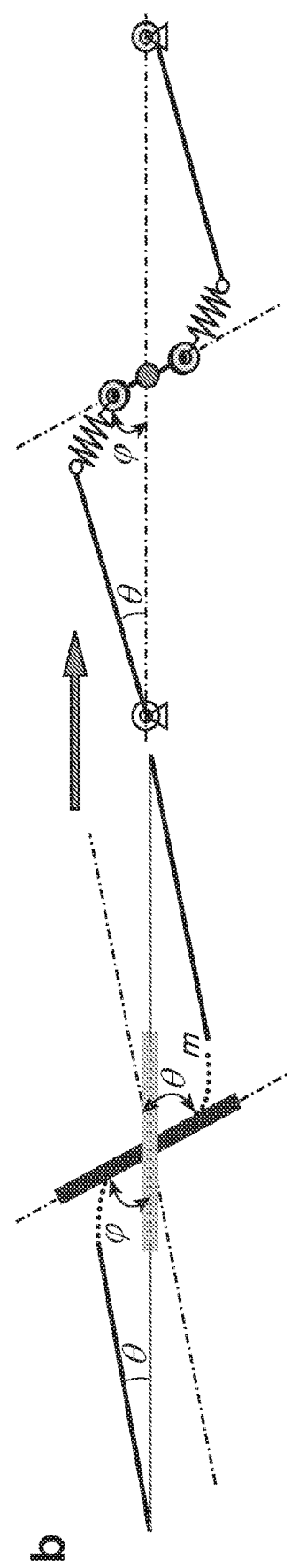
FIG. 7A
FIG. 7B

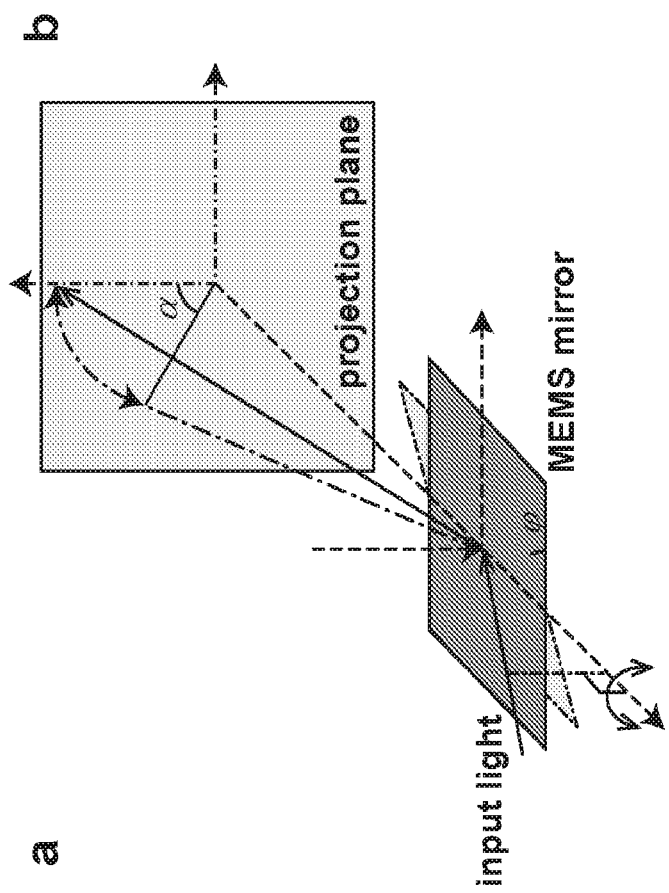
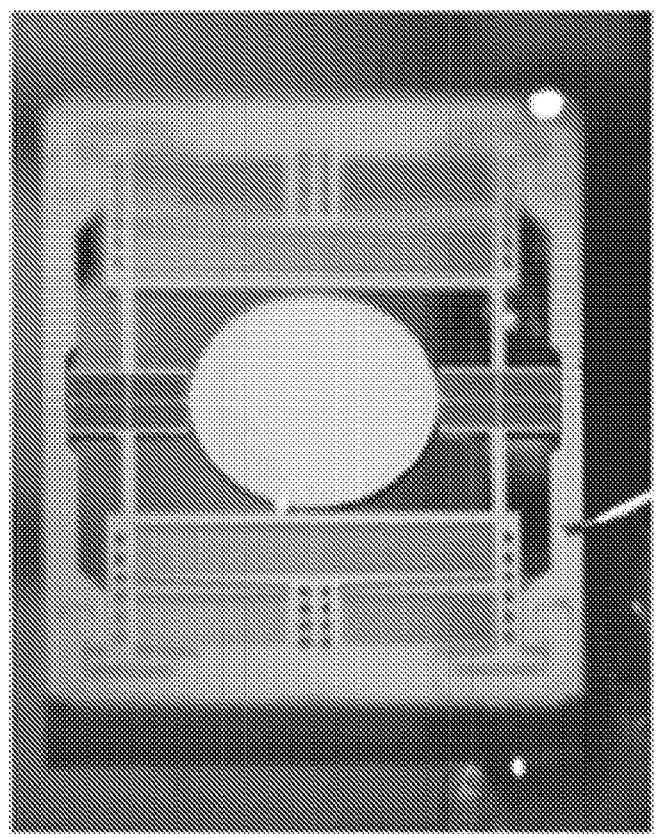
FIG. 11A
FIG. 11B

COMB-DRIVEN MEMS RESONANT SCANNER WITH FULL-CIRCUMFERENTIAL RANGE AND LARGE OUT-OF-PLANE TRANSLATIONAL DISPLACEMENT

CROSS-REFERENCE TO RELATED APPLICATIONS

This application claims priority to U.S. Provisional Patent Application No. 62/820,032, filed Mar. 18, 2019, which is hereby incorporated by reference in its entirety.

STATEMENT OF GOVERNMENT INTEREST

This invention was made with government support under EB020644 awarded by the National Institutes of Health. The government has certain rights in the invention.

FIELD OF THE DISCLOSURE

The disclosure relates generally to techniques for imaging tissue using an optical instrument and, more particularly, to techniques for allowing real-time scanning using an optical instrument.

BACKGROUND

The brief description of related technology provided herein is for the purpose of generally presenting the context of the disclosure. Work of the presently named inventor, to the extent it is described in this brief description of related technology section, as well as aspects of the description that may not otherwise qualify as prior art at the time of filing, are neither expressly nor impliedly admitted as prior art against the present disclosure.

Resonant devices fabricated with Micro Electro Mechanical Systems (MEMS) technology have been used to perform fast scanning with large amplitudes and low power consumption. MEMS technology is characterized by high mechanical reliability and has been used for applications that include projection display, light detection and ranging (LiDAR), three-dimensional (3D) depth sensing, and Fourier transform infrared (FTIR) spectroscopy. Using conventional MEMS designs and fabrication methods, resonant devices have been developed that can achieve optical scan angles up to 90°. While this level of performance is adequate for many applications, even larger displacements and deflection angles are needed for emerging directions, such as panoramic imaging and surround-view monitoring.

In response to the desire for larger displacements and deflection angles, multiple MEMS scanners with wide-angle optics have been attempted. The current designs, however, result in increased complexity and size. Other MEMS scanners have been proposed with actuation techniques that deploy large force or torque, motion conversion mechanisms, high fracture materials as flexible pivots, or vacuum packaging for reduced damping. In yet other proposed electrostatic, electromagnetic, and thin-film piezoelectric techniques show promise for low-cost batch fabrication capacity, and thus are increasingly common MEMS-based approaches used to increase scan range. The need for more effective MEMS scanners remains, especially for scanners that can achieve translational and torsional motion, as these allow for true three dimensional (3D) scanning to be performed.

Until now, designs for MEMS resonant scanners that have demonstrated large stroke are focused on either translational or torsional motions only. Only a few approaches, including thin-film piezoelectric and thermoelectric actuation mechanisms, can provide large amplitude motions in both modes. Deformable thin-film structures in piezoelectric and thermoelectric MEMS scanners are usually designed with sufficient length to provide large deformations at the expense of limited scan speeds. Electrostatic actuation offers advantages of fast response times, low power consumption, and ease of integration, despite limited operational range from the pull-in effect and from high actuation voltage requirements.

There is a need for improved MEMS resonant scanners that can be used for 3D and 2D imaging.

SUMMARY

To address the foregoing, the present application describes MEMS resonant scanner assemblies and devices deploying the same. The MEMS resonant scanner may be a comb-driven MEMS resonant scanner with optical scan angles greater than 360° under ambient pressure. In addition to this extraordinarily large scan range and rotation of movement, various examples herein are able to achieve large out-of-plane translation for axial scanning and volumetric imaging. In various examples, out-of-plane translations of greater than 100 μm, greater than 200 μm, greater than 300 μm, greater than 400 μm, and greater than 500 μm can be achieved. Total scan angles of greater than 100°, greater than 200°, greater than 300°, greater than 400°, greater than 500°, and so on, are achievable in the X-axis and Y-axis motion.

In accordance with an example, a scanning assembly for use in an optical instrument comprises: a frame providing support; a reflector suspended in the interior region of the frame; a folded-beam spring assembly coupled to the reflector and configured to provide deflection of the reflector for beam scanning in an out-of-plane direction; a lever suspension assembly coupled to a frame of the scanning assembly and coupled to the folded-beam spring assembly positioned between the lever suspension assembly and the reflector, the lever suspension assembly configured to provide torsional movement of the reflector for beam scanning over a two-dimensional region, the lever suspension assembly having lever arms; and a comb drive assembly connected to the lever suspension assembly for controlling torsional and/or translational movement of the reflector.

In some examples, the lever suspension assembly comprises a first lever suspension and a second lever suspension, each of the first and the second lever suspensions having lever arms being mechanically coupled to the frame of the scanning assembly and to the folded-beam spring assembly, each lever arm being flexible to provide for deflection of the reflector.

In some examples, each of the first lever suspension and the second lever suspension comprise H-shaped torsional springs.

In some examples, the folded-beam spring assembly comprises a first folded-beam spring assembly and a second folded-beam spring assembly each coupled to the reflector on opposing sides of the reflector and each configured to provide deflection of the reflector in an out-of-plane direction.

In some examples, each of the first folded-beam spring assembly and the second folded-beam spring assembly comprises four multi-turn central-clamped folded-beam springs connected to the reflector through a connection arm.

BRIEF DESCRIPTION OF THE DRAWINGS

For a more complete understanding of the disclosure, reference should be made to the following detailed description and accompanying drawing figures, in which like reference numerals identify like elements in the figures, and in which:

FIG. 7A illustrates a rigid-body model for translational (deflection) movement of a 3D scanner, in accordance with an example. FIG. 7B illustrates a rigid-body model for torsional (reflection) movement of a 2D scanner, in accordance with an example.

FIG. 8A illustrates a $1^{st}$ mode which is torsional (reflection), and occurs at a resonant frequency of 792.34 Hz. FIG. 8B illustrates a 2nd mode which is translational (deflection) and occurs at a resonant frequency of 1000.05 Hz.

FIG. 9A illustrates a deposition of plasma enhanced chemical vapor deposition (PECVD) $SiO_2$ hard mask layers. FIG. 9B illustrates a double side patterning. FIG. 9C illustrates deep-reactive-ion-etching (DRIE) etching. FIG. 9D illustrates buffered hydrofluoric acid (BHF) $SiO_2$ etching and releasing, rinsing and drying, and Al deposition.

FIGS. 11A and 11B illustrate a schematic depicting movement of a reflector of a 2D scanner and a picture of a reflector of the 2D scanner mounted on a substrate, respectively, in accordance with an example.

FIGS. 15A and 15B FIG. 10 illustrate scanner parameters, in particularly, showing a relationship between the drive voltage and frequency (FIG. 15A) and maximum vertical displacement and drive voltage (FIG. 15B), in accordance with an example.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, techniques for the design, fabrication, and performance of compact integrated two-dimensional (2D) MEMS scanners are provided. These 2D MEMS scanners have dimensions that allow them to be housed within endoscopic devices and other small form factor applications.

The 3D MEMS scanning techniques described herein are capable of producing both large angular deflections and out-of-plane displacement. For example, total scan angles of greater than approximately 100°, greater than approximately 200°, greater than approximately 300°, greater than approximate 400°, greater than approximately 500°, and so on, are achievable in the X-axis and Y-axis motion. The 2D MEMS scanner techniques described herein can achieve such operating conditions with scanning along the Z-axis at depths greater than approximately 200 μm, greater than approximately 300 μm, greater than approximately 400 μm, greater than approximately 500 μm, greater than approximately 600 μm, and so on, in vertical displacement.

Figure 1:
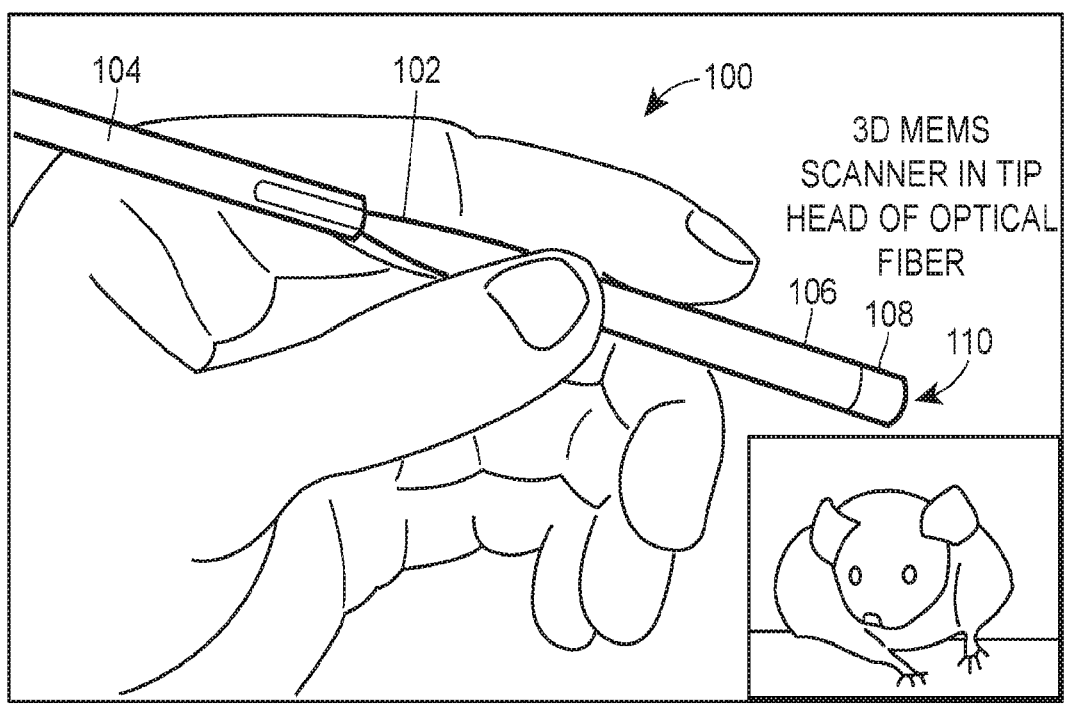
FIG. 1 depicts an optical probe having a proximal end and a distal end having a tip which houses a 2D scanner, in accordance with an example.
Figure 2:
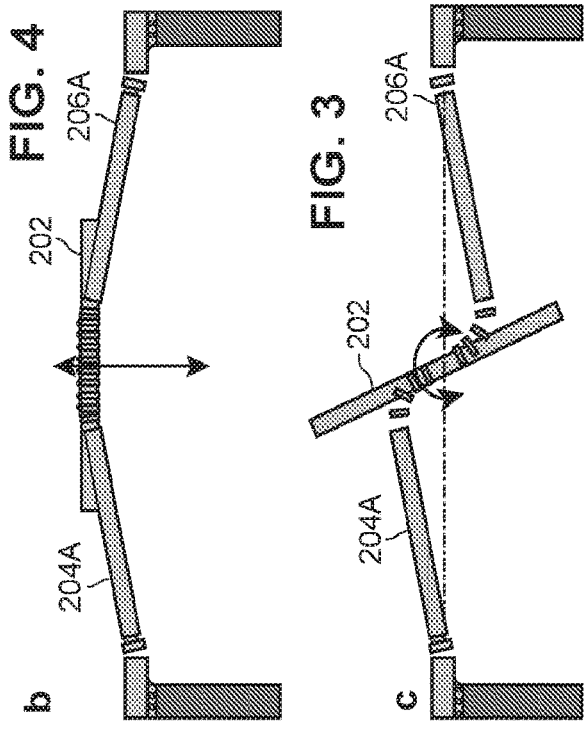
FIG. 2 is a top view of a 2D scanner, in accordance with an example.

FIG. 2 depicts an 2D optical scanner 200 in accordance with an example. The 2D optical scanner has three degrees of freedom, along each of the x-axis, the y-axis, and the z-axis. The 2D optical scanner 200 includes a mirror reflector 202 centered in a central region of the scanner 200. The reflector 202 may be coated with a reflective surface, reflective in the visible and/or infrared regions. In some examples, including endoscope environments, the reflector 202 has a diameter of 1.5 mm.

Figure 3:
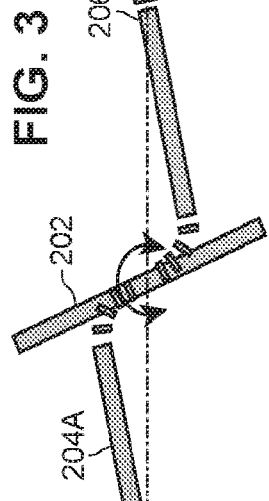
FIG. 3 is a side cross-sectional view of the 2D scanner of FIG. 2 showing torsional rotation, in accordance with an example.
Figure 4:
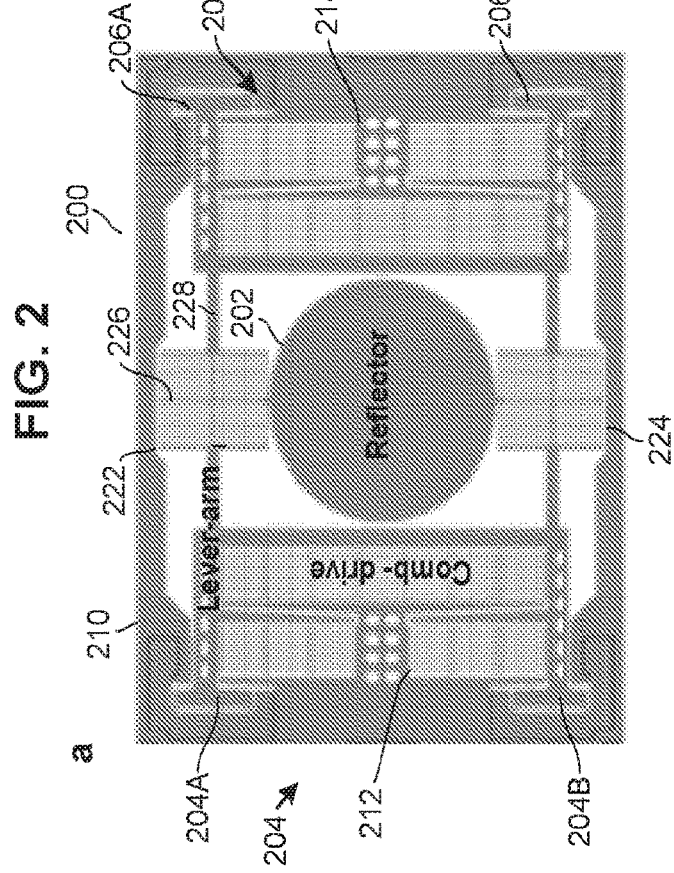
FIG. 4 is a side cross-sectional view of the 2D scanner of FIG. 2 showing out-of-plane translational displacement, in accordance with an example.

The reflector 202 is supported by two symmetrical lever-based suspensions 204 and 206, each having lever arms 204A, 204B, and 206A, 206B, respectively. These lever arms 204A, 204B, 206A, and 206B extend from a frame 210 of the scanner 200 and are flexible to provide compliance for moving the reflector 202 in a torsional (e.g., rotational) path (e.g., for scanning an XY-plane) and a deflection (e.g., linear out-of-plane displacement) path (e.g., for scanning along a Z-axis). FIG. 3 illustrates an example of torsional path deflection of the reflector 202 by use of lever arms. FIG. 4 illustrates an example of deflection path traversed by the reflector 202. That is, the scanner 200 includes a compliant mechanism formed by suspensions that provide a motion conversion function which enables out-of-plane displacement (deflection) and rotation (torsional movement), as shown in FIGS. 3 and 4.

Figure 5:
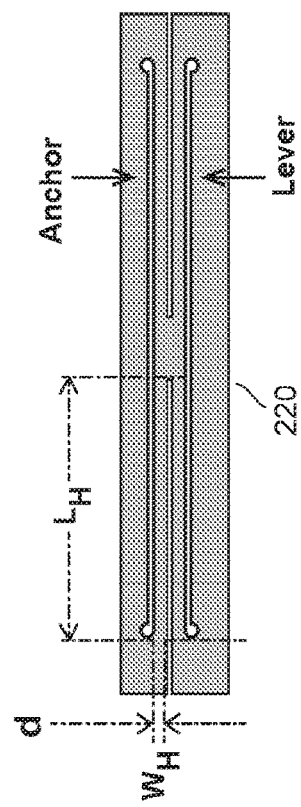
FIG. 5 is a top view of an example H-shaped torsional spring, which is attached to the chip frame as pivots, for moving the 2D scanner of FIG. 2, in accordance with an example.

Each of the lever arms 204A, 204B, 206A, and 206B are designed with a ladder-like geometry having a pair H-shaped torsional springs 220 that attach to the frame 210. FIG. 5 illustrates a top view of one of the H-shaped torsional springs 220 that is attached to the frame 210 and acts as a pivot for both torsional and deflection path movement of the reflector 202. The H-shaped torsional spring 220 is formed of partially overlapping grooves to facilitate movement, and is characterized by two different design geometries, a spacing width between adjacent grooves, $W_H$, and an overlap length, $L_H$. This example design of an H-shaped torsional spring enables large angular rotations while providing high resistance to lateral bending.

In the illustrated example, the suspension 204 and 206 are identical but disposed on opposite sides of the reflector 202 and patterned as reflected images of one another. Suspension 204 includes a comb drive 212. Suspension 206 includes comb drive 214. In the illustrated example, the comb drives 212 and 214 are multiple row comb drives.

Figure 6:
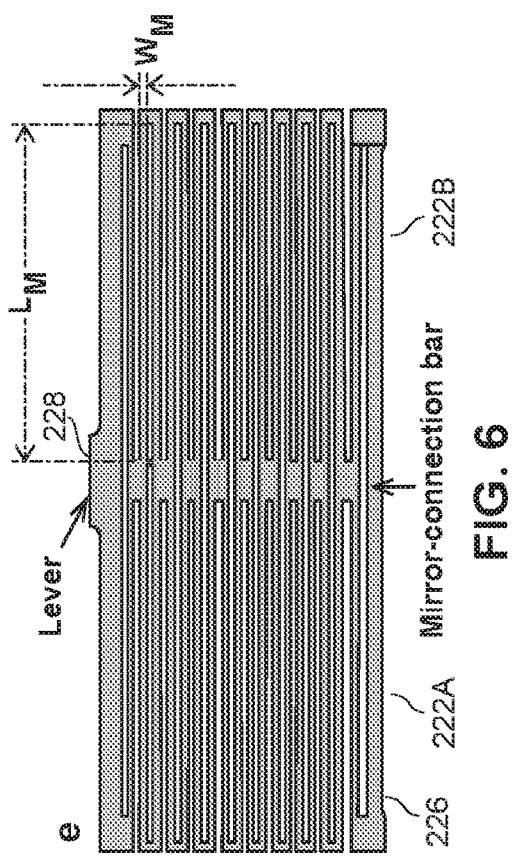
FIG. 6 is a top view of an example multi-turn central-clamped folded-beam spring for moving the 2D scanner of FIG. 2, in accordance with an example.

In addition to comb drives 212 and 214, the reflector 202 is moved by a pair of four multi-turn central-clamped folded-beam springs 222 and 224 that are used to transform motion and connect the reflector 202 with the lever arms 204A, 204B, 206A, and 206B. Half of the spring 222 is shown in FIG. 6, showing two folded-beam sides 222A and 222B, a connection arm 226 mechanically coupling to the reflector 202, and a lever connection end 228 for mechanically coupling to a level 204A. The design of these springs 222 and 224 enables large deflections in the folding direction while providing high resistance to lateral bending.

In operation, the two comb-drives 212 and 214 are formed as in-plane structures in a silicon layer of a silicon-on-insulator (SOI) wafer. The two drives 212 and 214 are used to excite the 3D scanner 200 at resonance. A two-row comb arrangement of the drives 212 and 214 provides for large electrostatic torque. A high ratio for either reflector translation or rotation to lever rotation is achieved by attaching the multi-turn central-clamped folded-beam springs 222 and 224 directly to the connection arm 226 along the central axis of the reflector 202. The vertical displacement along the Z-axis and the rotation (scan) angle of the reflector are dependent on not only the rotation of the lever arms 204 and 206 but also on the deformation of the multi-turn folded-beam springs 222 and 224.

Example rigid body models of a 2D scanner like that of scanner 200 are shown in FIGS. 7A and 7B, models that describe the motion of the reflector and levers. The multi-turn folded-beam spring is treated as a tension and torsion spring connected in series. The equation of motion can be expressed as follows:

$$z = z_L + z_m = L \times \sin\theta + \sum_i z_i \qquad (1)$$

$$\varphi = \theta_m - \theta = \sum_i \theta_i - \theta, \qquad (2)$$

where $z_L$ is the vertical displacement provided by the lever arm at its free end, $z_m$ is the vertical displacement provided by the multi-turn folded-beam spring, L is the entire length of the lever arm, $\theta$ is the rotation angle of the lever arm, and $\theta_m$ is the total bending angle generated by the multi-turn folded-beam spring at the central axis of the mirror. Finally, $z_i$ and $\theta_i$ are the vertical displacement and the torsional angle generated by individual beams of the multi-turn folded-beam spring, respectively.

Large vertical displacements and scan angles can be achieved using a design with long levers and soft springs, but at lower resonant frequencies. However, the ability to modify geometric parameters for multiple components in a lever-based compliant mechanism allows us for greater design flexibility to meet various amplitude and speed requirements. Applying equations (1) and (2), for example, we can achieve large vertical displacements and scan angles with a small rotation of the lever. The comb-drives between the lever arm and the scanner frame may be arranged to generate and impart large electrostatic torque throughout a significant portion of the oscillation period. In addition, since $z_i$ and $\theta_i$ are only a fraction of the vertical displacement and the torsional angle of the mirror, the risk of fracture caused by large deformations and stress is dramatically reduced, we have found, with the proposed designs.

The equations of motion for the 2D scanner 200 were derived using the Euler-Lagrange method. The equations for torsional motion are as follows in equations (3) and (4):

$$J_M \varphi'' + b_{Mr} \varphi' + 4k_{mt}(\varphi+\theta) = 0, \qquad (3)$$

where $J_M$ and $b_{Mr}$ are the inertia of the reflector and the damping coefficient in the torsional mode, respectively, and $k_{mt}$ is the equivalent torsional spring constant. The torsional motion of the lever arms is expressed as:

$$J_L \theta'' + b_L \theta' + 2k_L \theta = \qquad (4)$$
$$T_{es} + 2k_{me} \times L_O L \sin\theta \times \frac{\sqrt{(L\sin\theta)^2 + (L_O - L)^2} - (L_O - L)}{\sqrt{(L_O - L\cos\theta)^2 + (L\sin\theta)^2}}$$

where $J_L$ and $b_L$ are the inertia and damping coefficient of the lever arm, $k_L$ is the torsional spring constant of the H-shaped spring, $T_{es}$ is the electrostatic torque, $k_{me}$ is the equivalent extension spring constant of a single multi-turn central-clamped beam-folded spring, and $L_O$ is the distance from the pivot of the lever arm to the central axis of the reflector. The H-shaped spring may be located at one end of the lever arm and used as a pivot to connect to the anchor. The pivot is connected to the chip frame.

The equation for out-of-plane translational motion is as follows:

$$Mz'' + b_{Mt}z' + 4k_{me} \times \frac{(z - L\sin\theta)^2}{\sqrt{(z - L\sin\theta)^2 + (L_O - L\cos\theta)^2}} = 0 \quad (5)$$

where M is the mass of the reflector, $b_{Mt}$ is the damping coefficient of the reflector in the translational mode, and $k_{me}$ is the equivalent extension spring constant of a single multi-turn central-clamped beam-folded spring.

The 2D scanner structure was optimized using a finite element model (FEM) to achieve stable motion in the torsional and translational modes and to avoid crosstalk introduced by mechanical and electrical coupling. Geometric parameters of the H-shaped torsional spring, the multi-turn folded-beam spring, and lever arm, are shown, Table 1.

TABLE 1

Geometric parameters of scanner components.

| | Length | Width | Thickness | Turns |
|---|---|---|---|---|
| H-shape torsion spring | $L_H$ = 200 μm | $W_H$ = 10 μm | 50 μm | 1 |
| Multi-turn central-clamped folded-beam spring | $L_M$ = 400 μm | $W_M$ = 7 μm | 50 μm | 17 |
| Lever-arm | $L_A$ = 1475 μm | — | 50 μm | — |

Figure 8B:
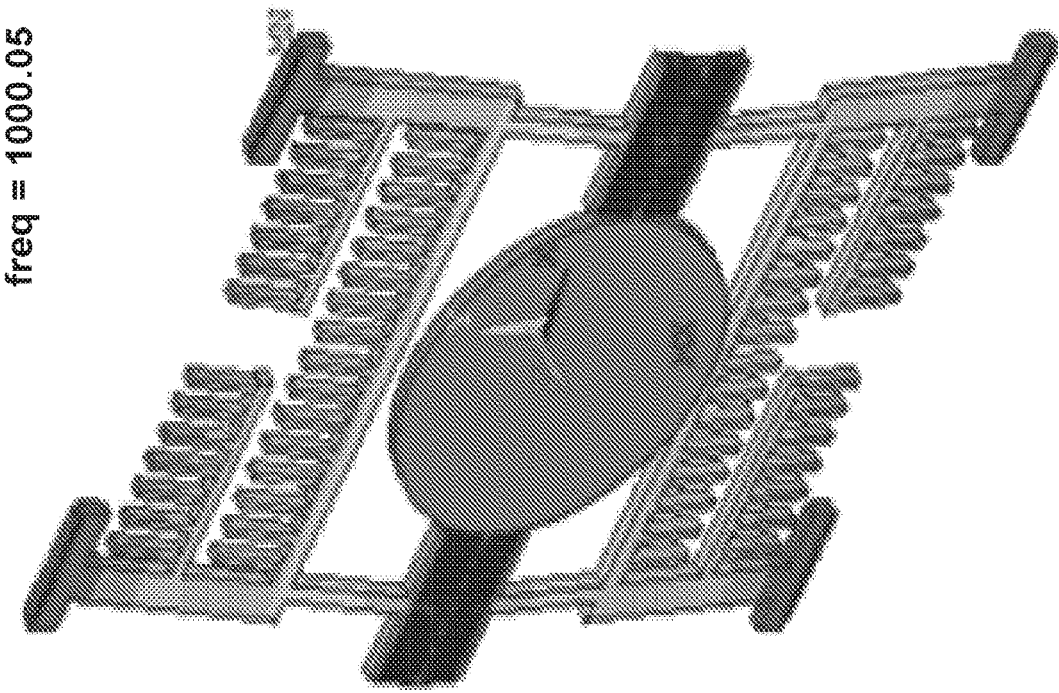
FIGS. 8A and 8B illustrate finite element model (FEM) modal analyses for a 2D scanner, in accordance with an example.
Figure 8A:
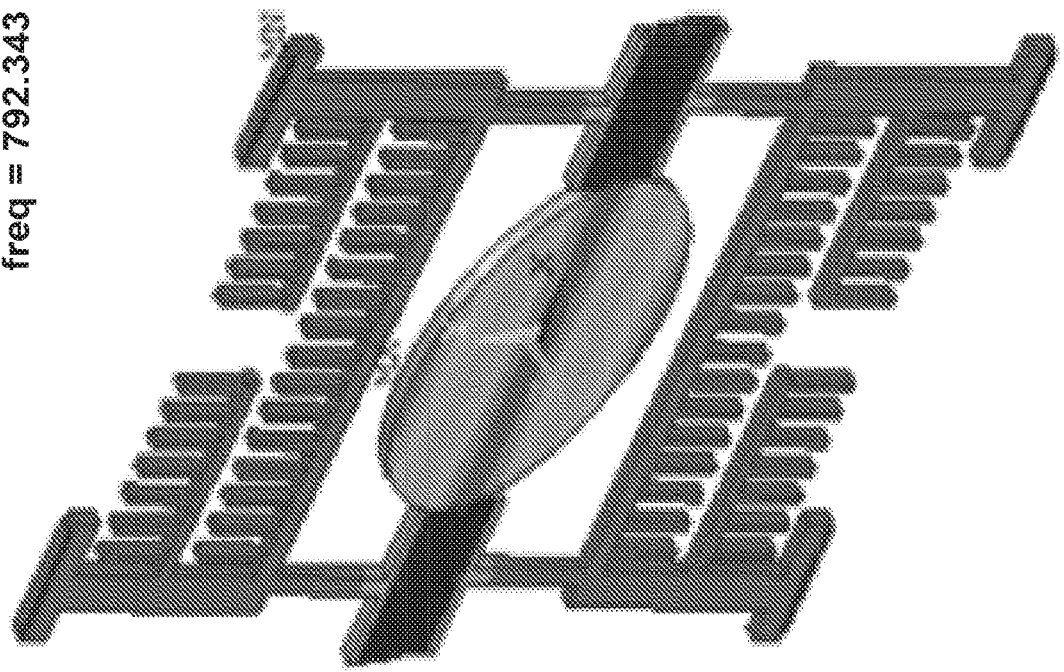

The results of the FEM modal analysis, in an example, are shown FIGS. 8A and 8B. The $1^{st}$ (FIG. 8A) and $2^{nd}$ (FIG. 8B) modes are torsional and translational, respectively, and occur at a resonance frequency of ~792 and ~1 Hz, respectively, as shown. In a parametric resonance system, large amplitude motion is achieved using a drive frequency that is twice that of the eigenfrequency. These results demonstrate that frequencies for different modes in an optimized scanner can be identified and designed to avoid crosstalk.

Example Fabrication & Device

Figure 9A:
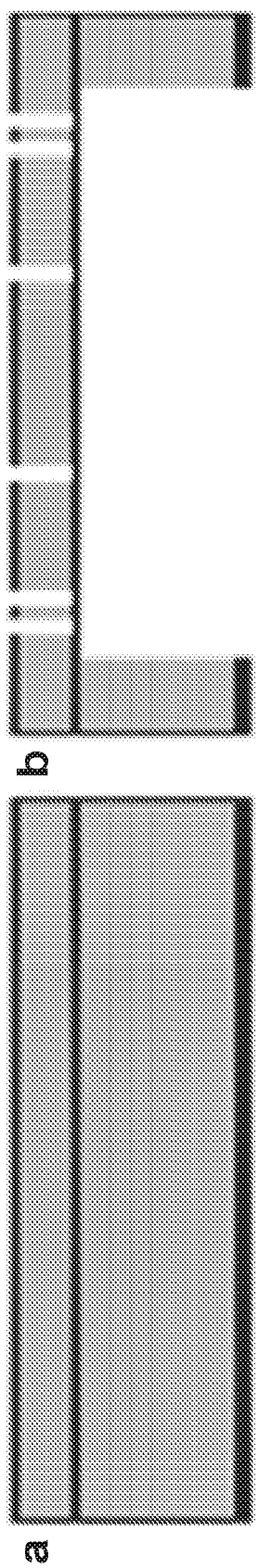
FIGS. 9A-9D illustrate different steps in a fabrication process for forming a 2D scanner, in accordance with an example.
Figure 9B:
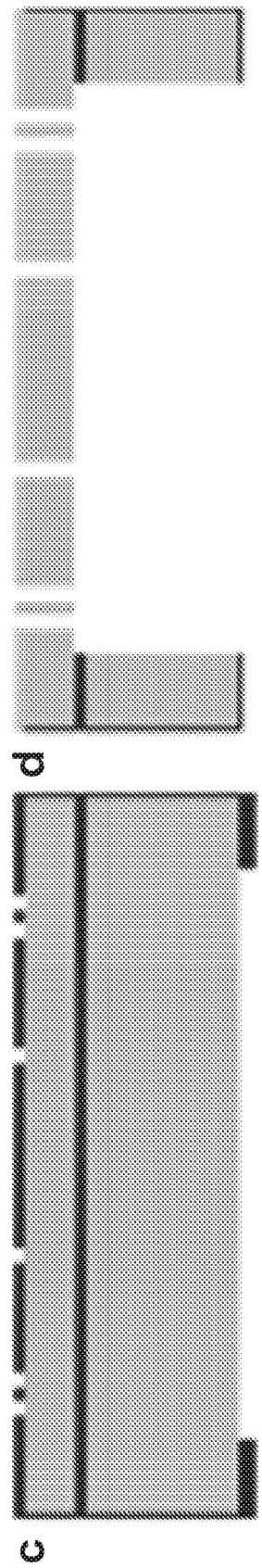
Figure 9C:
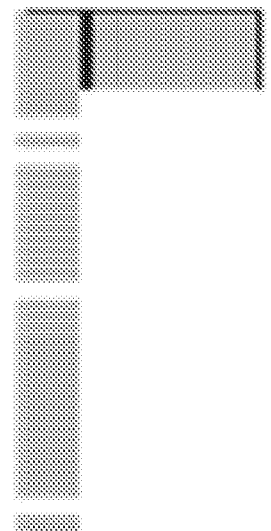
Figure 9D:

FIGS. 9A-9D illustrate example fabrication processes for forming a 3D scanner like that of scanner 200. In the illustrated example, a two mask process is used. A SOI wafer with a 50 μm silicon device layer, a 0.5 μm silicon dioxide ($SiO_2$) buried layer, and a 415 μm silicon handle layer are used. As shown in FIG. 9A, a 0.6 μm $SiO_2$ layer and a 2.5 μm $SiO_2$ layer are formed on the front and back side of a SOI wafer, respectively, using plasma enhanced chemical vapor deposition (PECVD). These layers form hard masks that are used to pattern structures and protect surfaces from scratches and contamination. Referring to FIG. 9B, the top and bottom surfaces of the SOI wafer are patterned by lithography with the top structure and backside mask, respectively. Referring to FIG. 9C, after removing the PECVD $SiO_2$ layers by plasma etching, the exposed silicon and handle layers are etched away using deep-reactive-ion-etching (DRIE). Referring to FIG. 9D, following a buffered hydrofluoric acid (BHF) etch process to remove the $SiO_2$ layers, an isopropyl alcohol (IPA) rinse and dry process is performed to release the movable structures. Finally, a ~60 nm aluminum (Al) layer is coated on the bare surface of the silicon device layer using an electron beam evaporation process.

Figure 10A:
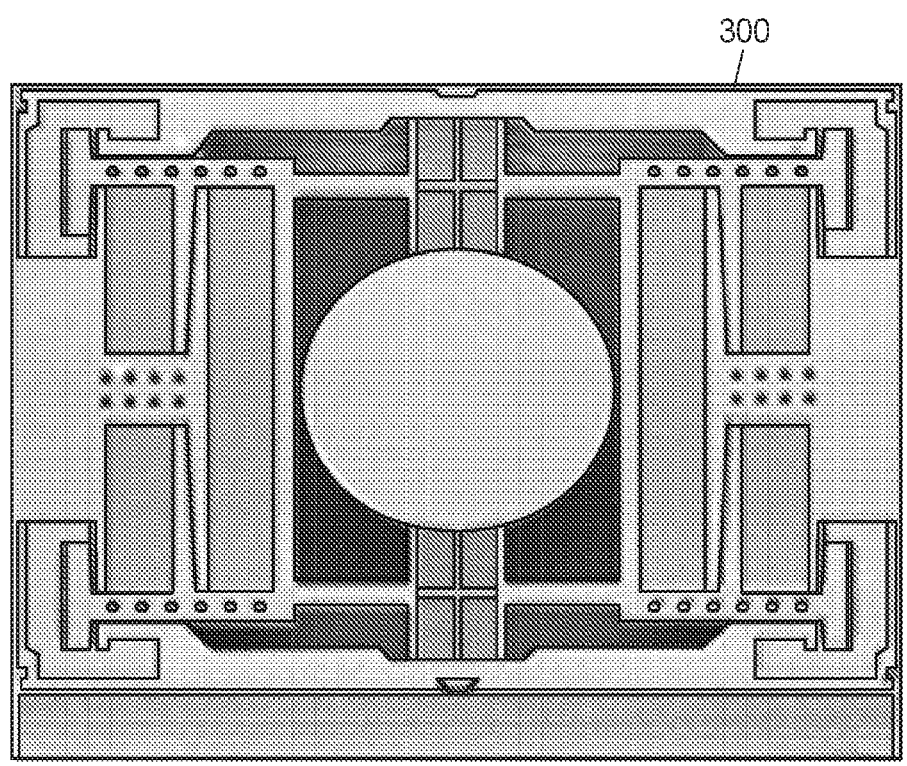
FIGS. 10A-10C illustrate scanning electron microscope (SEM) pictures of an example 2D scanner, H-shaped spring of a lever arm, and a multi-turn central-clamped folded-beam spring, respectively.
Figure 10B:
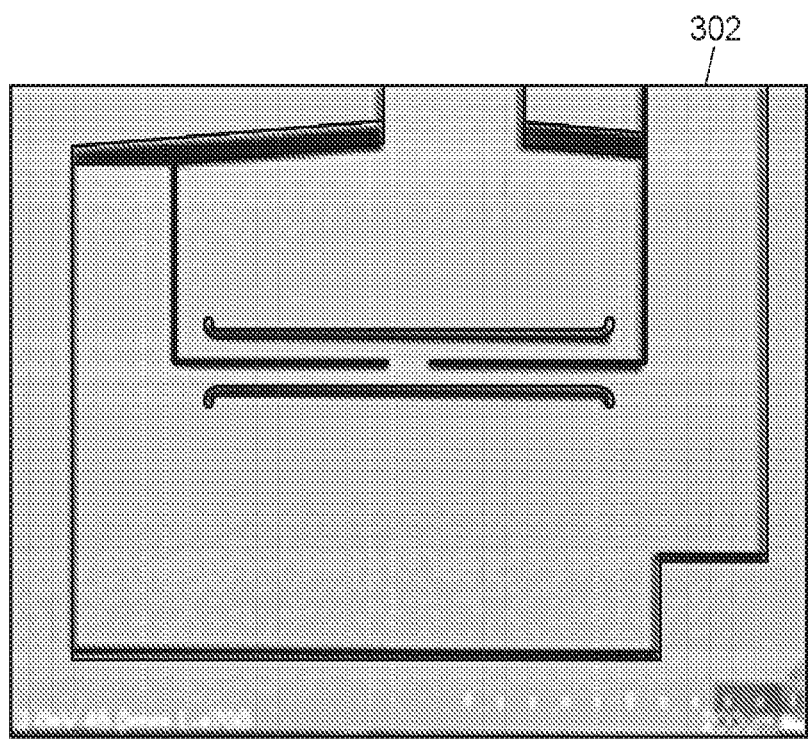
Figure 10C:
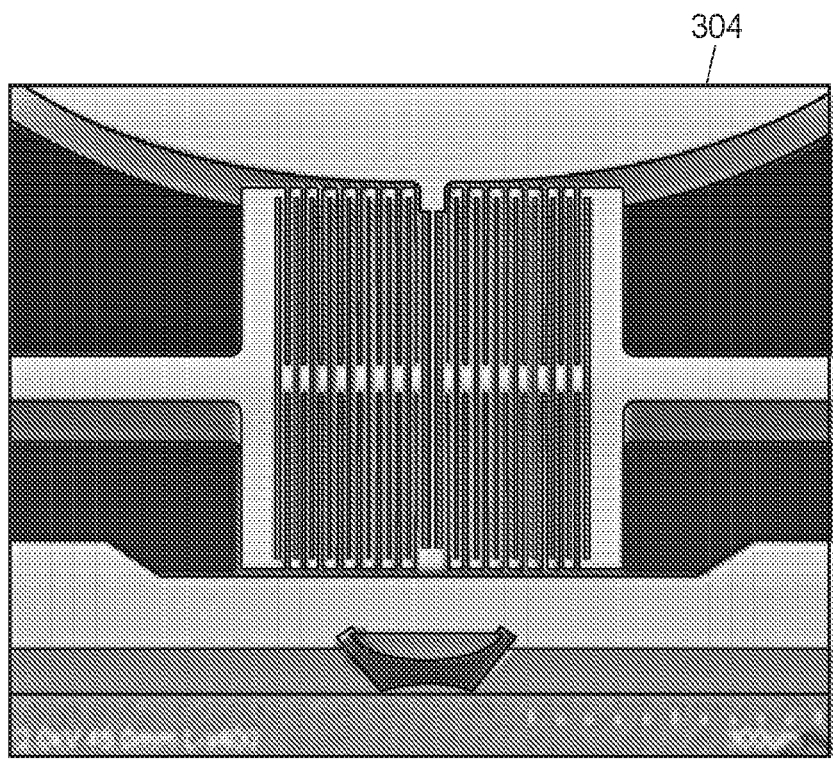

FIGS. 10A-10C provide scanning electron microscope (SEM) images of an example 3D scanner showing an overall view of a 2D scanner 300, H-shaped springs 302, and multi-turn central-clamped folded-beam spring 304, respectively. The dynamic performance of the 3D scanner 300 was characterized by sweeping the drive frequency to electrostatically activate the resonant modes. Laser scanning was used to measure the optical scan angle 2φ. This parameter was measured as the interior angle of the arc scan α projected in a plane perpendicular to the torsional axis of the mirror reflector, as shown in FIG. 11A. The fabricated device was mounted on the substrate along one edge only, as shown in FIG. 11B. This arrangement prevented the mounted substrate from blocking deflected light in the oscillating torsional mode and reduced squeeze damping in the oscillating out-of-plane translational mode. A displacement sensor was used to measure mirror reflector travel in the translational mode.

Figures 12A, 12B:
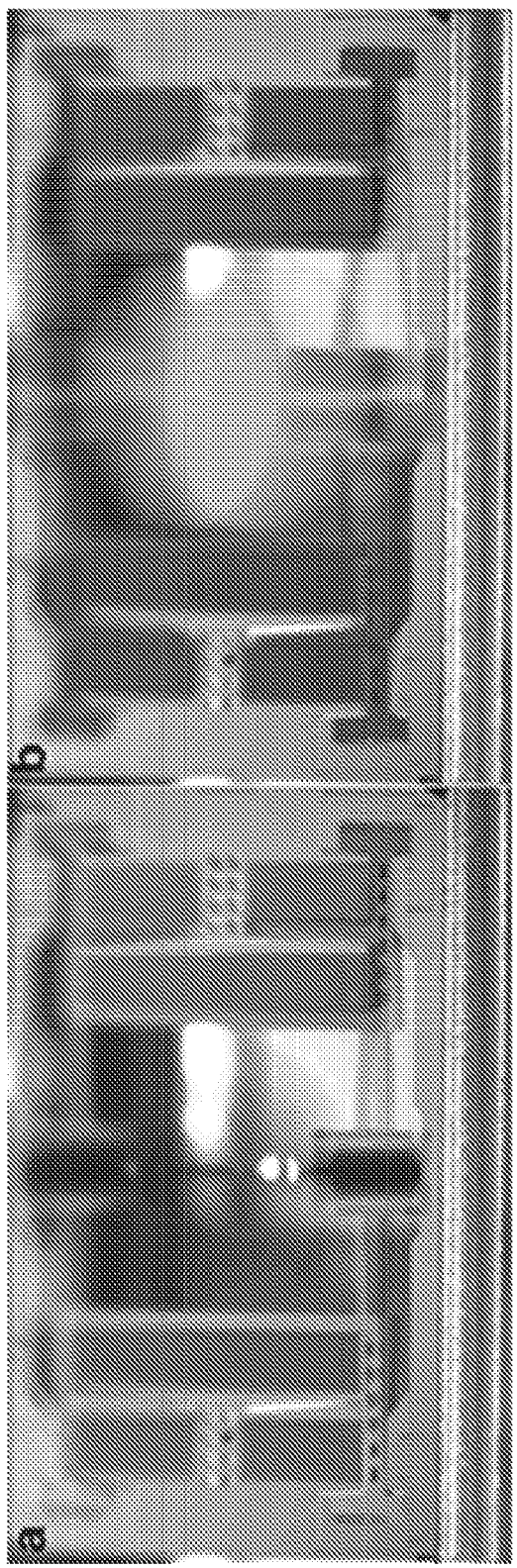
FIGS. 12A and 12B illustrate pictures of a 2D scanner motion, showing (a) Torsional mode with ~±90° mechanical scan angle and (b) Out-of-plane translational mode with displacement >466 μm (thickness of device chip), respectively, in accordance with an example.
Figure 13:
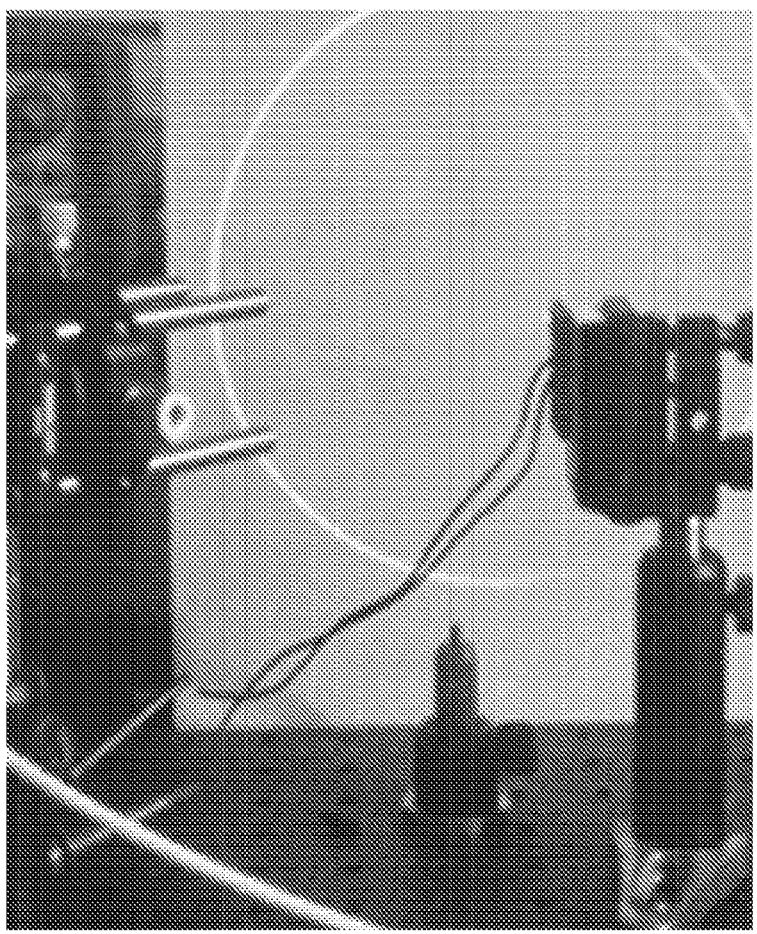
FIG. 13 illustrates an example rotational scan angle that may be achieved by a 2D scanner, in accordance with an example.
Figure 14A:
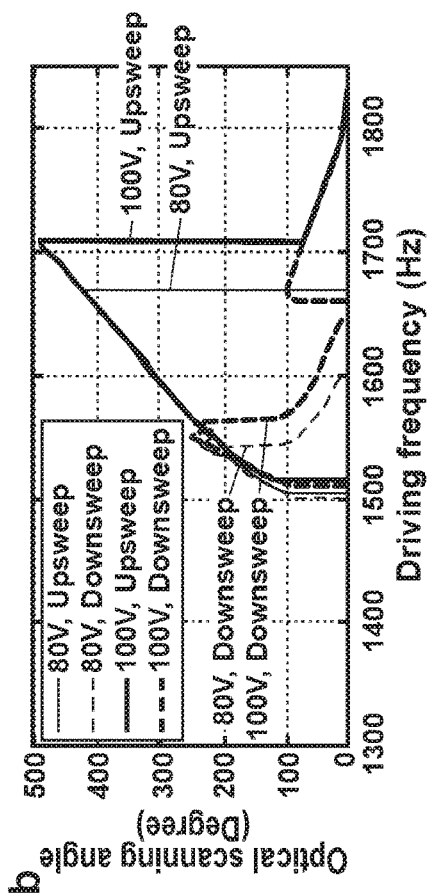
FIGS. 14A-14D are plots of frequency response, showing primary and secondary super-harmonic resonances (FIG. 14A), an example achieving a maximum optical scan angle of 494° at 1.707 kHz using 100V (FIG. 14B), Large scan angles up to 205° may be achieved near $10\omega t_0$ using 80V (FIG. 14C), and an unstable region disappears when upsweep (low-to-high frequencies) and downsweep (high-to-low frequencies) of frequency response curves coincide near 62 $\omega t_0$ at 80V (FIG. 14D), in accordance with an example.
Figure 14B:
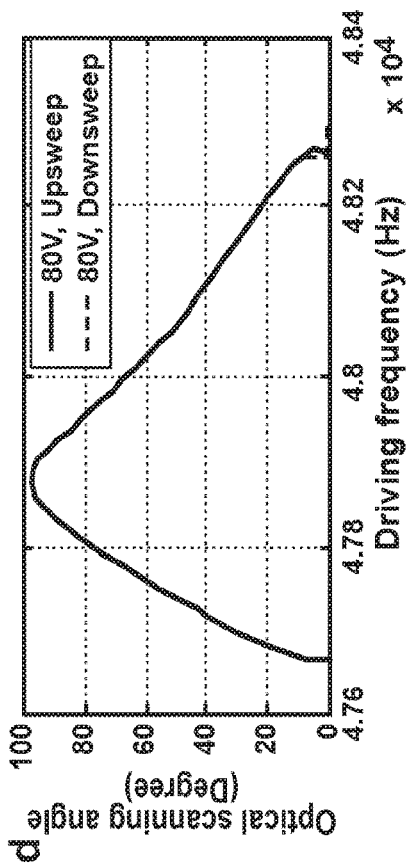
Figure 14C:
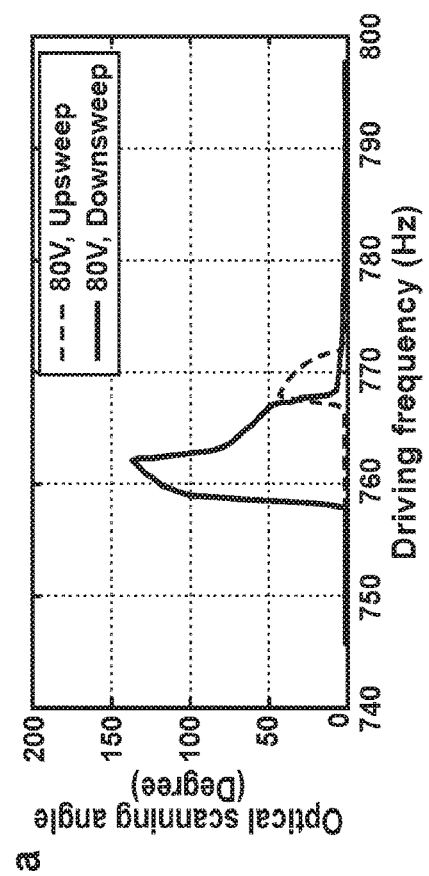
Figure 14D:
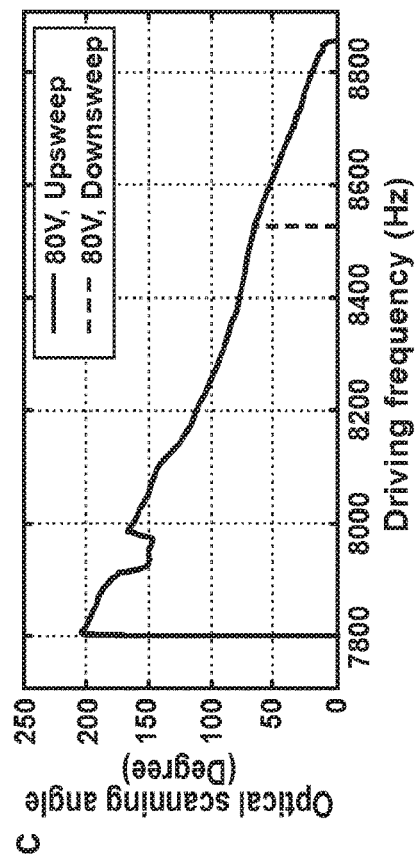

Motion of the 2D scanner 300 in an example, is shown in the resonant torsional mode with a ±90° mechanical scan angle (FIG. 12A), and in the resonant out-of-plane translational mode with displacement >466 μm, (FIG. 12B). In this example, the 2D scanner generates a wide rotational scan angle, as shown by the full circumferential pattern of a reflected laser beam, FIG. 13.

FIGS. 14A-14D illustrate torsional motion performance for the example 2D scanner 300. As we show, the 2D scanner, acting as a parametrical resonance scanner, can exhibit profound non-linear behavior in the torsional mode. The response to a square-wave drive signal at frequencies near twice the natural frequency ($\omega_{t0}$) shows a stiffness hardening-softening-mixed behavior, and a maximum optical scan angle of 494° is achieved at 1.707 kHz and 100V, FIG. 14B. Other high-order super-harmonic resonances were observed in addition to this second super-harmonic and primary resonance, see, FIG. 14A. The stiffness-softening phenomenon is seen when the frequency of a sine-wave drive signal is near $10\omega_{t0}$ at 80V, and a large scan angle up to 205° is achieved, see, FIG. 14C. However, the unstable region disappears when the upsweep and downsweep of the frequency response curves coincide using a sine wave drive signal at a frequency near $62\omega_{t0}$ at 80V, see FIG. 14D. While this performance data is provided by way of example, it shows the robustness and wide optical scanning angle range and the tunability of that range that can be achieved with the present designs.

Figure 15A:
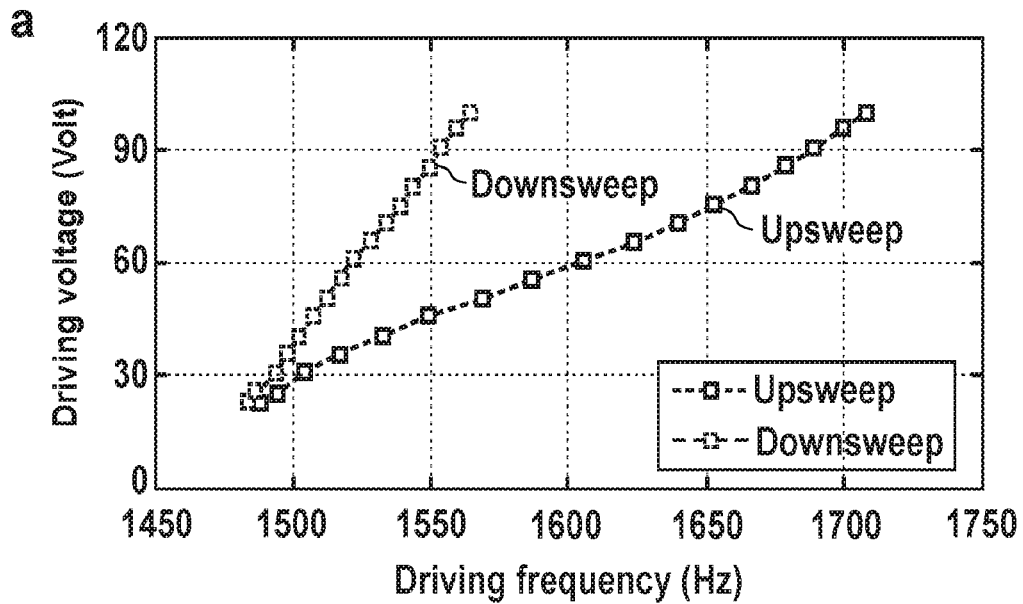
Figure 15B:
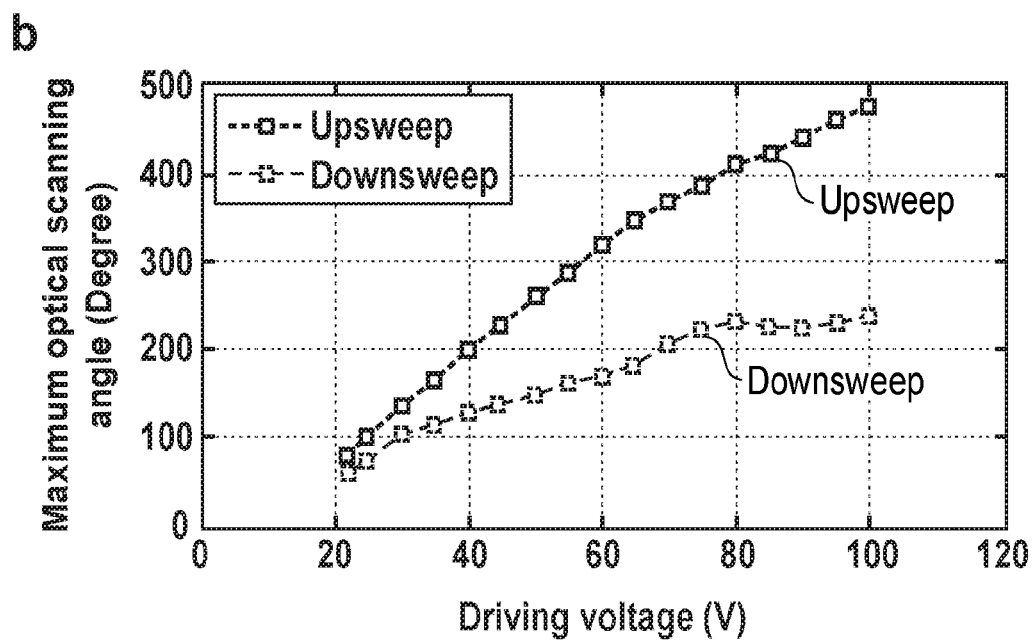
Figure 16B:
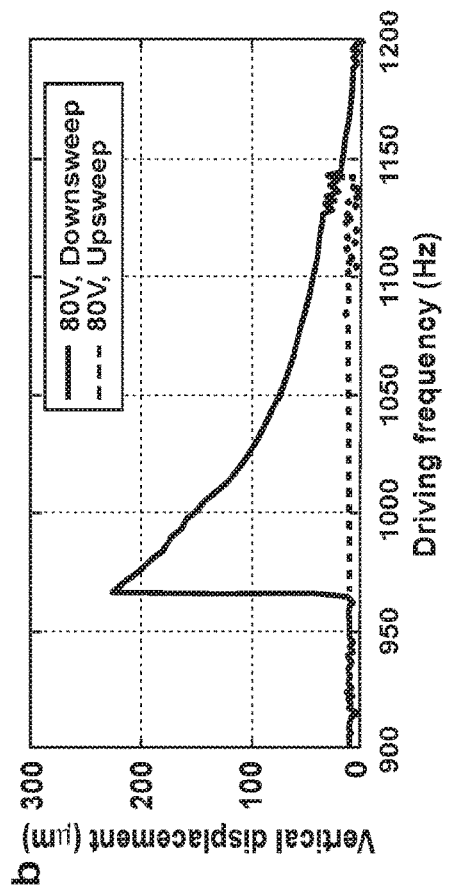
FIGS. 16A-16D illustrate plots of frequency response of a 2D scanner for translational motion, in accordance with an example, and under different driving frequency conditions.
Figure 16D:
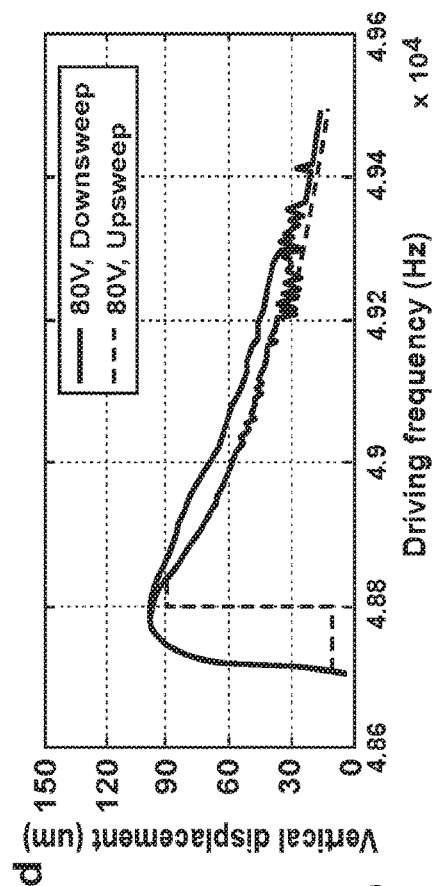
Figure 16A:
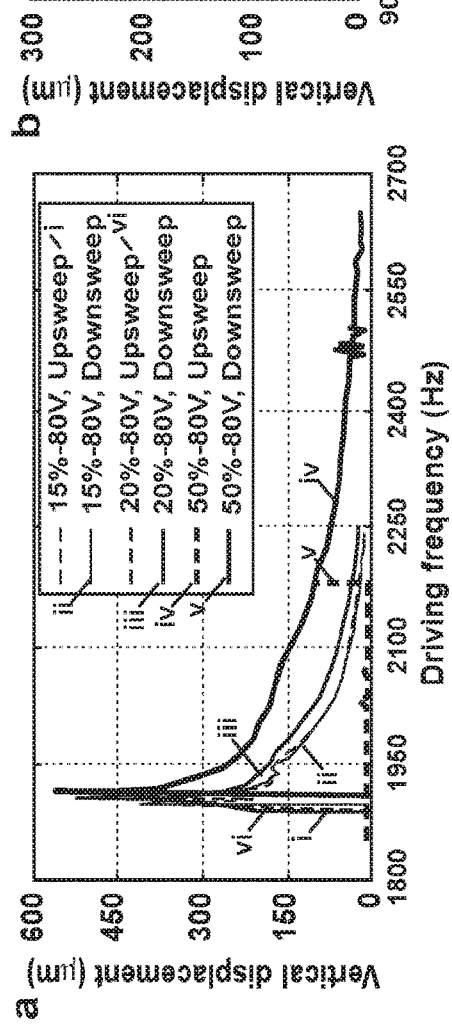
Figure 16C:
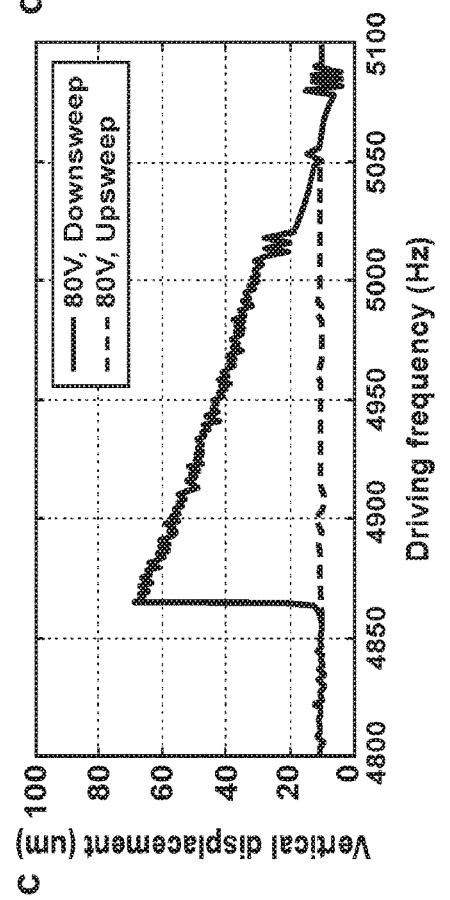

The relationship among drive frequency, voltage, and maximum optical scan angle using a square wave signal and 50% duty cycle near twice of the natural frequency of the torsional mode, is shown in FIG. 15A. An optical scan angle of ~200° is achieve at 40V is shown in FIG. 15B.

Figure 17A:
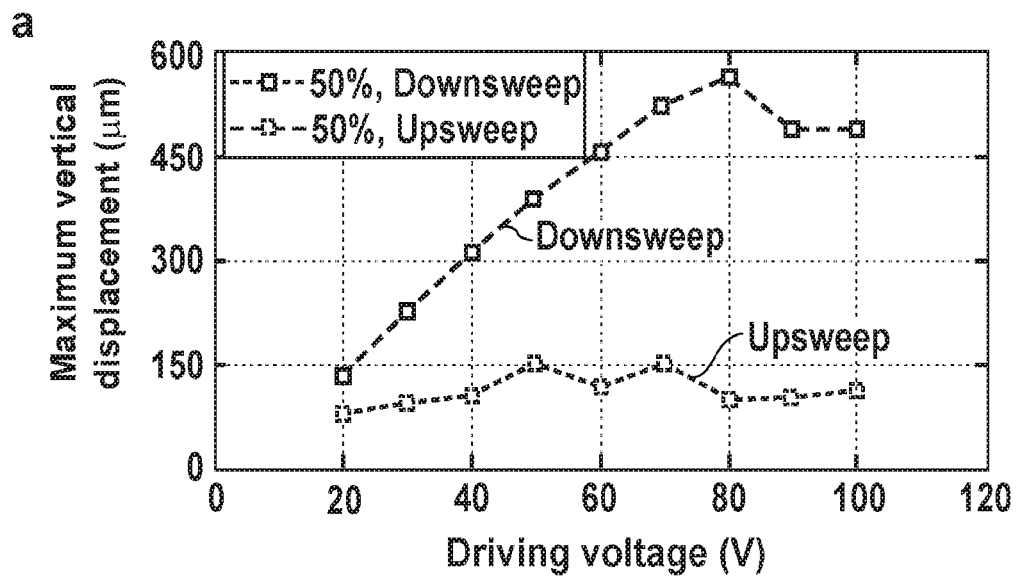
FIGS. 17A and 17B illustrate the relationship of drive frequencies, drive voltages and maximum optical scan angle for translational mode, showing the relationship between drive voltage and frequency (FIG. 17A), and the relationship between the maximum vertical displacement and drive voltage (FIG. 17B), in accordance with an example.
Figure 17B:
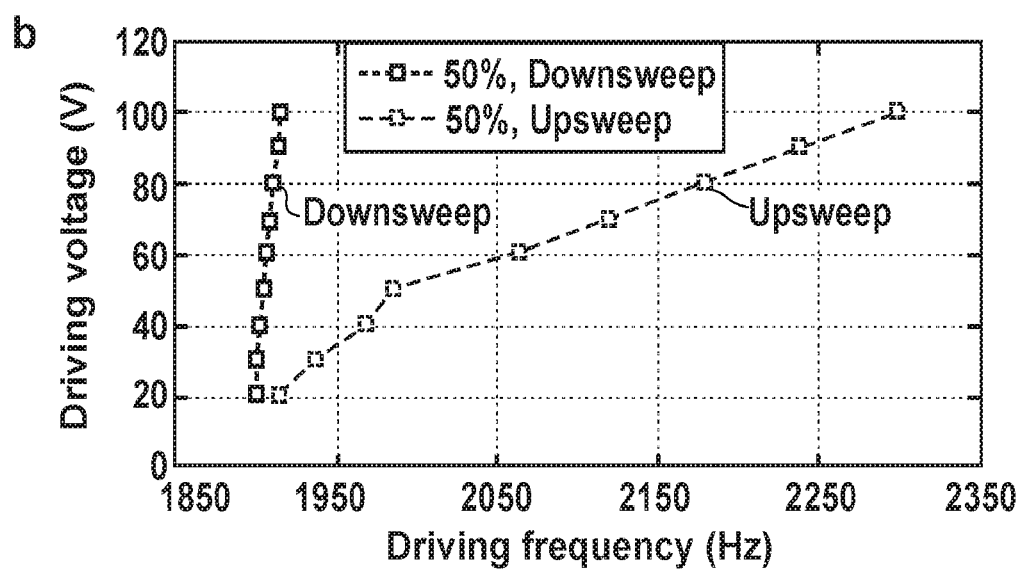

Out-of-plane Translational Motion Performance: In some examples, the 2D scanners demonstrate a stiffness hardening-softening-mixed behavior in the translational (deflection or out-of-plane) mode. High-order super-harmonic resonances are also observed, as shown in FIGS. 16A-16D, which show vertical displacement measured from a neutral reflector position under different drive frequency conditions. An example of the relationship among drive frequency, voltage, and maximum displacement with a square-wave signal and 50% duty-cycle sweeping frequency near twice the natural frequency of the translational mode is shown, FIGS. 17A and 17B. A maximum vertical displacement of 561 μm is obtained with a downsweep in drive frequency of a square-wave with 50% duty-cycle near 1912 Hz at 80V. A displacement of ~310 μm is obtained with a low drive voltage of 40V.

The performance values provided are by way of example. We examined other device configurations of the scanner techniques herein, with similar results in 3D and 2D scanning. In an example, a 2D scanner was formed with a 0.7 mm diameter mirror that performs out-of-plane translational displacement of ~320 µm at 4.405 kHz and torsional scan with ~±90° mechanical scan angles at 8.425 kHz was developed. In another example, a 2D scanner with a 3 mm diameter mirror that performs out-of-plane translational scans with ~780 µm displacement at 652 Hz and torsional scans with ~±90° mechanical scan angles at 188 Hz was developed. In another example, 3D scanner that performed switchable horizontal/vertical 2D scanning was developed, capable of generating a dense Lissajous scan pattern in a horizontal 2D scanning mode.

The present techniques provide a comb-driven MEMS resonant 2D scanner based on a lever-based compliant mechanism for either torsional or (out-of-plane) translational scanning. The designs herein are able to achieve ultra-large scan ranges in ambient pressure with little risk for mechanical fracture. Further, the design of the lever-based compliant mechanisms is quite flexible.

The design and fabrication of high-speed MEMS scanners for optical applications is very challenging. Over the past 40 years, little progress has been made in the amplitude for deflection angle and translational displacement for most MEMS scanners. Optical instruments typically require large mirror dimensions to capture maximum light. Thus, large forces and torques are needed to achieve high scan amplitudes at fast speeds. Also, air damping increases significantly with larger mirror size and faster scan speeds. that require compact chip dimensions.

Although relatively high voltages are required to obtain large scan range. The present techniques, applying comb-driven devices, demonstrate high performance, including fast scan speeds with extraordinarily large amplitudes without use of vacuum packaging, low power consumption, compact size, and ease of fabrication. This level of performance may be deployed in miniature optical systems, including endoscopic devices, to perform panoramic imaging and surround-view monitoring. Furthermore, because the actuator is placed between the chip frame and the lever-arm and its motion is only a fraction of the motion of the reflect, it is reasonable to expect to integrate the proposed lever-based compliant into MEMS resonant scanners that employ other actuation techniques, such as thin-film piezoelectric and electromagnetic actuation to achieve ultra-large scan range with low driving voltage.

Figure 18:
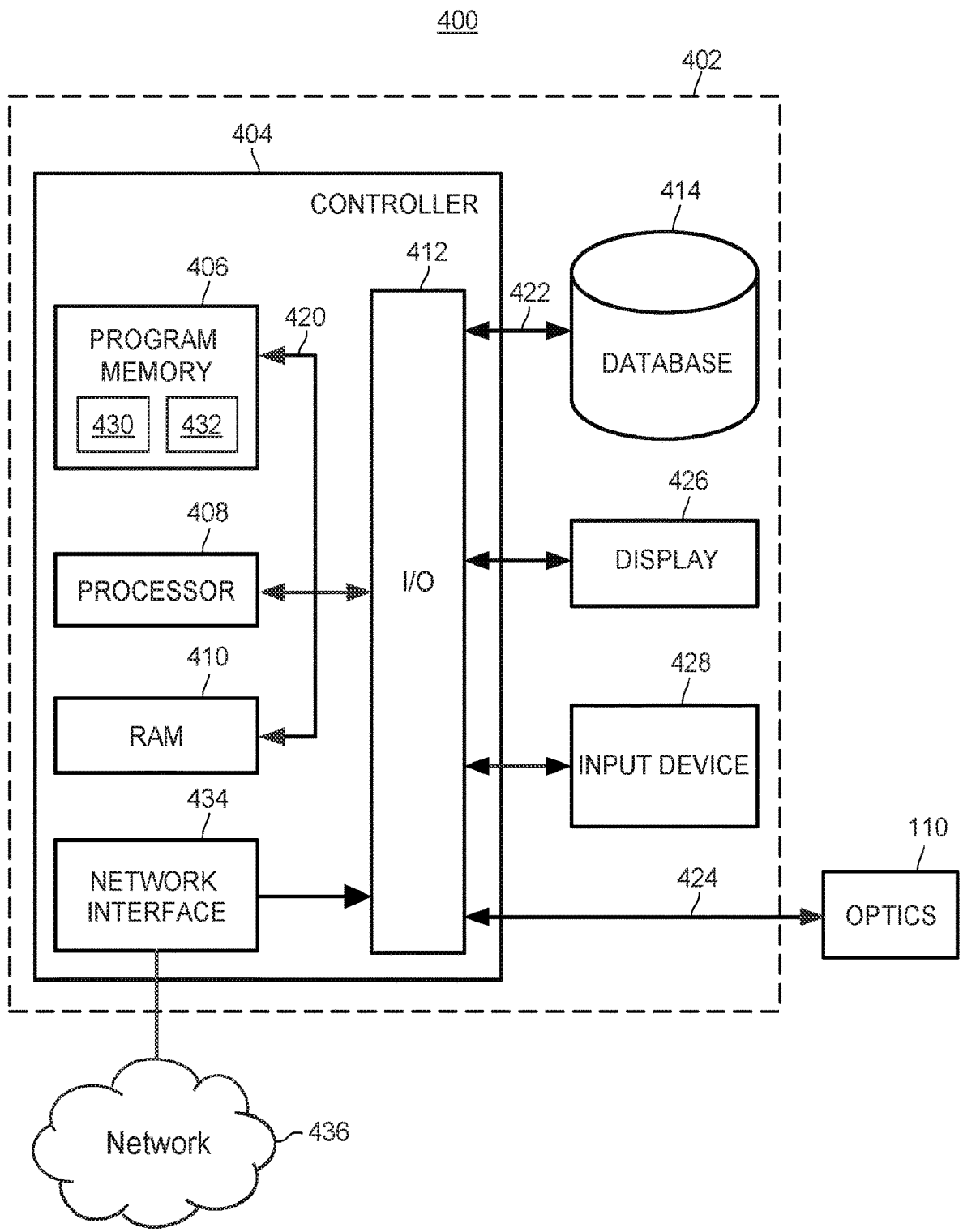
FIG. 18 depicts an example block diagram illustrating various components used in implementing an exemplary embodiment of the 2D scanner, in accordance with an example.

FIG. 18 is illustrates a system 400 illustrating the various components used in implementing an example embodiment of the 2D MEMS scanner discussed herein. A device 402 may have a controller 404 operatively connected to the database 414 via a link 422 connected to an input/output (I/O) circuit 412. It should be noted that, while not shown, additional databases may be linked to the controller 404 in a known manner. The controller 404 includes a program memory 406, the processor 408 (may be called a microcontroller or a microprocessor), a random-access memory (RAM) 410, and the input/output (I/O) circuit 412, all of which are interconnected via an address/data bus 420. It should be appreciated that although only one microprocessor 408 is shown, the controller 404 may include multiple microprocessors 408. Similarly, the memory of the controller 404 may include multiple RAMs 410 and multiple program memories 406. Although the I/O circuit 412 is shown as a single block, it should be appreciated that the I/O circuit 412 may include a number of different types of I/O circuits. The RAM(s) 410 and the program memories 406 may be implemented as semiconductor memories, magnetically readable memories, and/or optically readable memories, for example.

The program memory 406 and/or the RAM 410 may store various applications (i.e., machine readable instructions) for execution by the microprocessor 408. For example, an operating system 430 may generally control the operation of the device 402 (including the 3D scanner 110) and provide a user interface to the testing apparatus to implement the processes described herein. The program memory 406 and/or the RAM 410 may also store a variety of subroutines 432 for accessing specific functions of the device 402. The program memory 406 and/or the RAM 410 may further store data related to the configuration and/or operation of the device 402, and/or related to the operation of one or more subroutines. For example, the data may be data gathered by the 3D scanner 110, data determined and/or calculated by the processor 408, etc. In addition to the controller 404, the device 402 may include other hardware resources. The device 202 may also be coupled to various types of input/output hardware such as a visual display 426 and input device(s) 428 (e.g., keypad, keyboard, etc.) to fine tune actuation of the torsional and translation scanning. In an embodiment, the display 426 is touch-sensitive, and may cooperate with a software keyboard routine as one of the software routines 432 to accept user input. In some examples, the device 202 may communicate with connected devices through a wired or wireless network interface 434 connected to a communication network 436.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed:

1. A scanning assembly for use in an optical instrument, the scanning assembly comprising:
    a frame providing a support;
    a reflector suspended in an interior region of the frame for scanning a beam of the optical instrument;
    a folded-beam spring assembly coupled to the reflector and configured to provide deflection of the reflector for beam scanning in an out-of-plane direction;
    a lever suspension assembly coupled to a frame of the scanning assembly and coupled to the folded-beam spring assembly positioned between the lever suspension assembly and the reflector, the lever suspension assembly configured to provide torsional movement of the reflector for beam scanning over a two-dimensional region, the lever suspension assembly having lever arms, wherein the lever suspension assembly comprises a first lever suspension and a second lever suspension, each of the first and the second lever suspensions having lever arms being mechanically coupled to the frame of the scanning assembly and to the folded-beam spring assembly, each lever arm being flexible to provide for deflection of the reflector; and a comb drive assembly connected to the lever suspension assembly for controlling torsional and/or translational movement of the reflector.

2. The scanning assembly of claim 1, wherein the each of the first lever suspension and the second lever suspension comprise H-shaped torsional springs.

3. The scanning assembly of claim 1, wherein the folded-beam spring assembly comprises a first folded-beam spring assembly and a second folded-beam spring assembly each coupled to the reflector on opposing sides of the reflector and each configured to provide deflection of the reflector in an out-of-plane direction.

4. The scanning assembly of claim 1, wherein each of the first folded-beam spring assembly and the second folded-beam spring assembly comprises four multi-turn central-clamped folded-beam springs connected to the reflector through a connection arm.

5. The scanning assembly of claim 1, wherein the folded-beam spring assembly and the lever suspension assembly are configured to scan the beam over a scan angle of greater than 100°.

6. The scanning assembly of claim 1, wherein the folded-beam spring assembly and the lever suspension assembly are configured to scan the beam over a scan angle of greater than 200°.

7. The scanning assembly of claim 1, wherein the folded-beam spring assembly and the lever suspension assembly are configured to scan the beam over a scan angle of greater than 300°.

8. The scanning assembly of claim 1, wherein the folded-beam spring assembly and the lever suspension assembly are configured to scan the beam over a scan angle of greater than 400°.

9. The scanning assembly of claim 1, wherein the folded-beam spring assembly and the lever suspension assembly are configured to scan the beam over a scan angle of greater than 500°.

10. The scanning assembly of claim 1, wherein the folded-beam spring assembly and the lever suspension assembly are configured to scan the beam in the out-of-plane direction by greater than 200 µm.

11. The scanning assembly of claim 1, wherein the folded-beam spring assembly and the lever suspension assembly are configured to scan the beam in the out-of-plane direction by greater than 300 µm.

12. The scanning assembly of claim 1, wherein the folded-beam spring assembly and the lever suspension assembly are configured to scan the beam in the out-of-plane direction by greater than 400 µm.

13. The scanning assembly of claim 1, wherein the folded-beam spring assembly and the lever suspension assembly are configured to scan the beam in the out-of-plane direction by greater than 500 µm.

14. The scanning assembly of claim 1, wherein the folded-beam spring assembly and the lever suspension assembly are configured to scan the beam in the out-of-plane direction by greater than 600 µm.

* * * * *